United States Patent [19]

Jensen et al.

[11] Patent Number: 5,676,686
[45] Date of Patent: Oct. 14, 1997

[54] PACEMAKER WITH VASOVAGAL SYNCOPE DETECTION

[75] Inventors: Donald Nick Jensen, Roseville; Michael F. Hess, Minneapolis, both of Minn.

[73] Assignee: Medtronic, Inc., Minneapolis, Minn.

[21] Appl. No.: 637,579

[22] Filed: Apr. 25, 1996

Related U.S. Application Data

[63] Continuation of Ser. No. 309,222, Sep. 20, 1994, abandoned, which is a continuation-in-part of Ser. No. 246,647, May 20, 1994, abandoned.

[51] Int. Cl.$^6$ ............................................. A61N 1/362
[52] U.S. Cl. ............................................................ 607/9
[58] Field of Search ......................................... 607/9, 23

[56] References Cited

U.S. PATENT DOCUMENTS

| | | |
|---|---|---|
| 4,030,510 | 6/1977 | Bowers ................................. 607/9 |
| 4,556,063 | 12/1985 | Thompson . |
| 4,796,620 | 1/1989 | Imran ................................. 128/706 |
| 5,127,404 | 7/1992 | Wyborny . |
| 5,284,491 | 2/1994 | Sutton . |
| 5,377,190 | 12/1994 | Moulton ................................. 128/705 |
| 5,441,525 | 8/1995 | Shelton et al. ......................... 607/23 |
| 5,540,728 | 7/1996 | Shelton et al. ......................... 607/23 |

Primary Examiner—William E. Kamm
Attorney, Agent, or Firm—Harold R. Patton; Michael B. Atlass

[57] ABSTRACT

A method and apparatus for cardiac pacing, which provides for delivery of pacing pulses at an increased rate in response to a detected rapid drop in heart rate. A rapid drop may be detected in response to a drop of greater than a defined amount from the highest detected heart rate, over a preceding time period. Alternatively, an unbroken sequence of pacing pulses delivered at a base pacing rate may trigger pacing at an increased pacing rate.

28 Claims, 5 Drawing Sheets

| Top Rate (bpm) | Drop Size (bpm) | | | | | | | | |
|---|---|---|---|---|---|---|---|---|---|
| | 10 | 15 | 20 | 25 | 30 | 35 | 40 | 45 | 50 |
| 30 | NP | NP | NP | NP | NP | NP | NP | NP | NP |
| 35 | 72 | NP | NP | NP | NP | NP | NP | NP | NP |
| 40 | 54 | 99 | NP | NP | NP | NP | NP | NP | NP |
| 45 | 42 | 75 | 118 | NP | NP | NP | NP | NP | NP |
| 50 | 34 | 59 | 118 | 133 | NP | NP | NP | NP | NP |
| 55 | 28 | 47 | 90 | 103 | 146 | NP | NP | NP | NP |
| 60 | 23 | 39 | 71 | 82 | 113 | 156 | NP | NP | NP |
| 65 | 20 | 33 | 58 | 67 | 91 | 123 | 165 | NP | NP |
| 70 | 16 | 28 | 48 | 56 | 75 | 99 | 130 | 173 | NP |
| 75 | 14 | 24 | 40 | 47 | 63 | 82 | 106 | 137 | 180 |
| 80 | 13 | 21 | 34 | 40 | 53 | 69 | 88 | 112 | 143 |
| 85 | 11 | 18 | 30 | 35 | 46 | 59 | 74 | 93 | 117 |
| 90 | 10 | 16 | 26 | 31 | 40 | 51 | 63 | 79 | 98 |
| 95 | 9 | 14 | 23 | 27 | 35 | 44 | 55 | 68 | 83 |
| 100 | 8 | 13 | 20 | 24 | 31 | 39 | 48 | 59 | 71 |
| 105 | 7 | 12 | 18 | 22 | 28 | 34 | 42 | 51 | 62 |
| 110 | 7 | 11 | 16 | 20 | 25 | 31 | 38 | 46 | 55 |
| 115 | 1 | 10 | 15 | 18 | 22 | 28 | 34 | 41 | 18 |
| 120 | 1 | 1 | 13 | 16 | 20 | 25 | 30 | 36 | 43 |
| 125 | 1 | 1 | 1 | 15 | 19 | 23 | 28 | 33 | 39 |
| 130 | 1 | 1 | 1 | 1 | 17 | 21 | 25 | 30 | 35 |
| 135 | 1 | 1 | 1 | 1 | 1 | 19 | 23 | 27 | 32 |
| 140 | 1 | 1 | 1 | 1 | 1 | 1 | 21 | 25 | 29 |
| 145 | 1 | 1 | 1 | 1 | 1 | 1 | 1 | 23 | 27 |
| 150 | 1 | 1 | 1 | 1 | 1 | 1 | 1 | 1 | 25 |
| 155 | 1 | 1 | 1 | 1 | 1 | 1 | 1 | 1 | 1 |

FIG. 6

PACEMAKER WITH VASOVAGAL SYNCOPE DETECTION

This is a continuation of application Ser. No. 309,222 filed Sep. 20, 1994, now abandoned, which in turn is a continuation in part of application Ser. No. 08/246,647 filed on May 20, 1994 now abandoned.

FIELD OF THE INVENTION

The present invention relates to artificial cardiac pacemakers generally and more particularly to pacemakers for the treatment of patients who experience vasovagal syncope episodes and other effects from vasodepressor or cardioinhibitory disorders, such as carotid sinus syndrome.

BACKGROUND OF THE INVENTION

Vasovagal syncope is a condition marked by a sudden drop in heart rate and blood pressure, resulting in fainting. It is not only unpleasant for a patient, but potentially dangerous, as fainting may lead to injuries from falls. U.S. Pat. No. 5,284,491, issued to Sutton et al. on Feb. 8, 1994 and incorporated herein by reference in its entirety discloses a cardiac pacemaker specifically adapted to treat patients suffering from vasovagal syncope. In particular, the pacer detects when the patient's heart rate drops below a lower "hysteresis" rate and determines whether the average rate of decrease in the patient's heart rate, over a defined number of heartbeats or a defined time interval prior to reaching the "hysteresis" rate, is greater than a preset value. If so, the pacer's rate is set equal to the "hysteresis" rate and thereafter increased to an "intermediate" rate substantially higher than the "hysteresis" rate. The pacer's rate remains at the intermediate" rate for a preset time period and thereafter gradually declines to a lower pacing rate.

SUMMARY OF THE INVENTION

The present invention is directed toward an improved pacemaker for the treatment of patients with vasovagal syncope. The pacemaker of the present invention differs from the prior pacer disclosed in the Sutton patent primarily in that the method of detection of an episode of vasovagal syncope is refined. The therapy provided, in the form of an increased pacing rate, followed by fallback to a lower pacing rate, is retained.

Rather than simply detecting a rapid rate drop to a rate below a defined threshold rate or drop rate, as discussed above in conjunction with the Sutton patent, a persistent or stable rate below the threshold rate must be detected, prior to initiating pacing at an increased rate. A persistent or stable heart rate may be detected, for example, as a series of a predetermined number of beats below the drop rate. In a preferred embodiment, the vasovagal syncope detection function is disabled during a defined sleep period, so that rate drops associated with sleep do not result in inappropriate triggering of pacing at an increased rate.

Also in a preferred embodiment, the detection of rate drop employs a process for defining the highest persistent rate over a period of time preceding the fall of the heart rate below the drop rate. The heart rate is monitored over a series of time intervals, with the fastest two beat sequence in each time interval identified. The rate of the slower of the two beats in the identified sequence is stored as a "top rate", and the fastest of the "top rates" is identified as the highest persistent rate. The measured rate drop is then taken as the difference between the fastest such "top rate" and the rate following drop of the heart rate below the drop rate. This process prevents short intervals as might result from premature depolarizations of the atrium or ventricle from erroneously triggering pacing at an increased rate.

Also in a preferred embodiment, an alternative method of detecting vasovagal syncope and triggering an increased pacing rate is provided. The pacer in this embodiment keeps count of successive paced beats, and, in response to an extended series of paced beats at the base pacing rate, triggers an increased pacing rate.

BRIEF DESCRIPTION OF THE DRAWING

The various figures of the drawings are briefly described as follows:

FIG. 6 is a look-up table used by the pacer to detect drops in heart rate.

DETAILED DESCRIPTION OF THE PREFERRED EMBODIMENT

Figure 1:
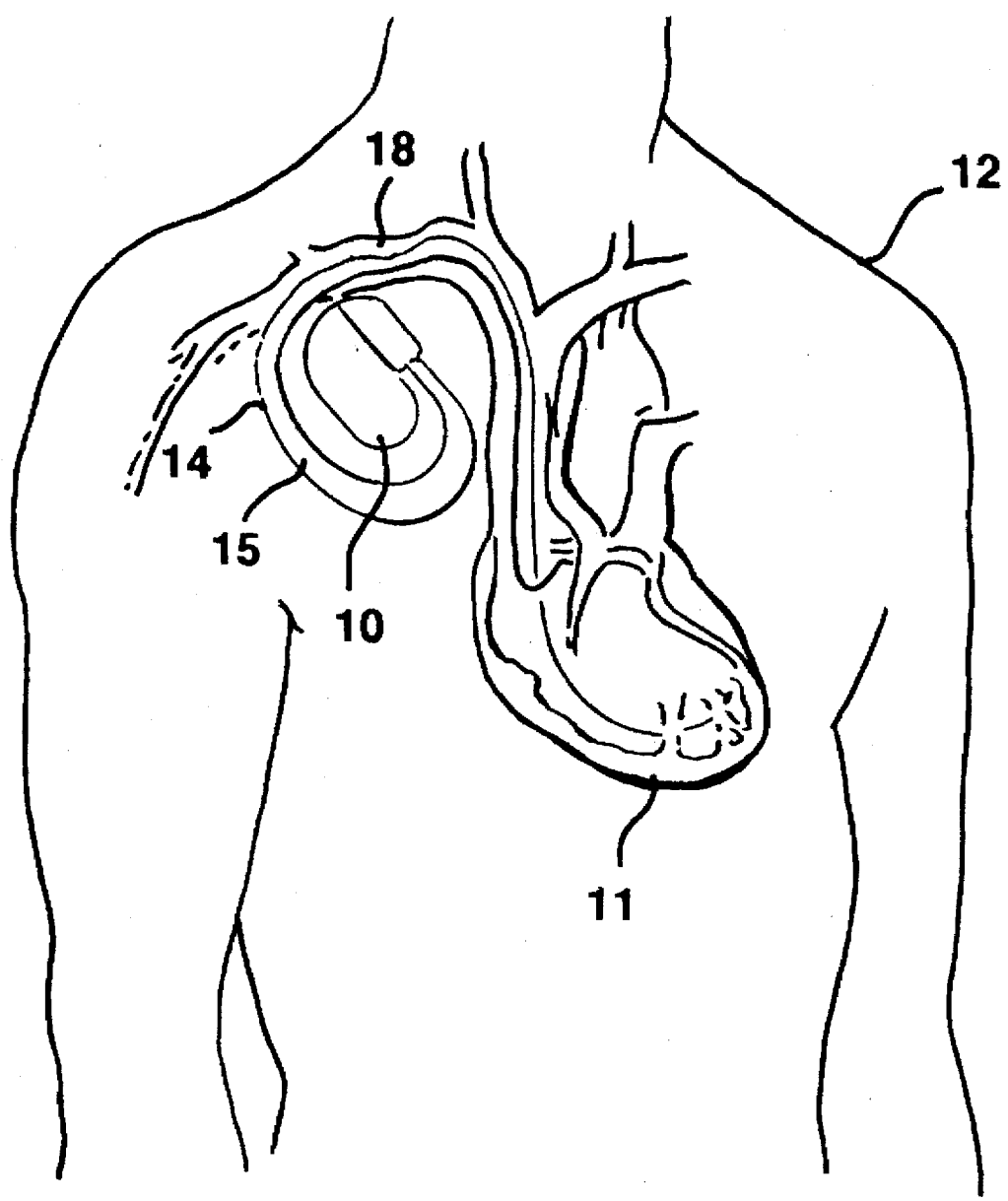
FIG. 1 is a diagram showing the heart of a patient electrically connected to the pacemaker in FIG. 2.

FIG. 1 generally shows a pacemaker 10, of a type suitable for practicing the present invention, implanted in a patient 12. The pacer illustrated is a dual chamber, rate responsive pacemaker, capable of sensing demand for cardiac output and of pacing the atrium and ventricle, but the invention may also be practiced in conjunction with non-rate responsive pacemakers and pacemakers which pace and/or sense in only one chamber of the heart. The pacemaker is provided with leads 14 and 15, which electrically couple the pacemaker 10 to the ventricle and atrium, respectively, of the patient's heart 11 via electrodes located thereon. The electrodes are employed to sense depolarizations of the heart, referred to informally herein as "beats" and to deliver pacing pulses to the heart.

Figure 2:
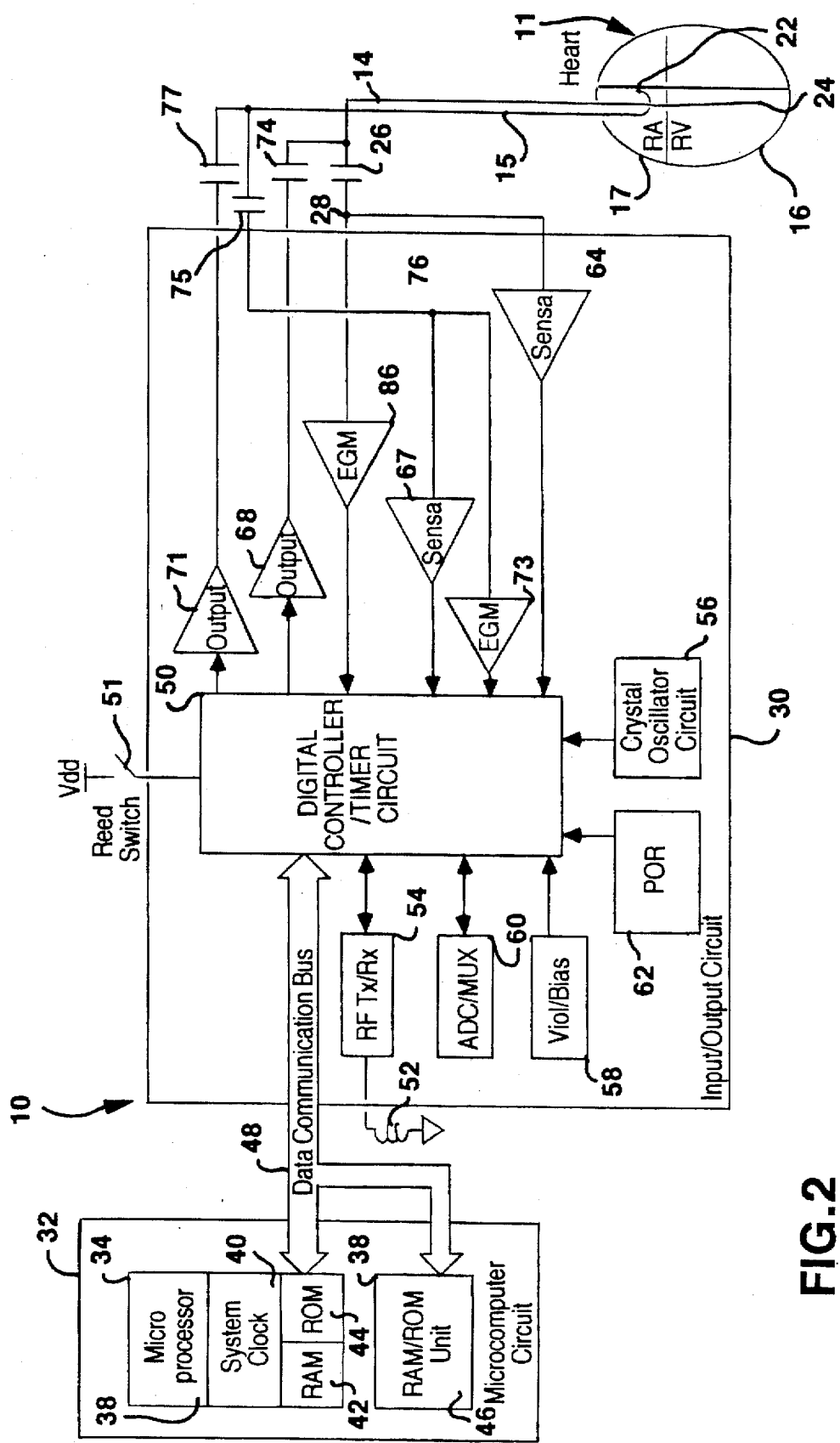
FIG. 2 is a schematic block diagram of an implantable pacemaker in which the present invention may be practiced.

FIG. 2 is a block circuit diagram illustrating a multiprogrammable, implantable, dual-chamber, bradycardia pacemaker 10 capable of carrying out the present invention. Although the present invention is described in conjunction with a microprocessor-based architecture, it will be understood that it could be implemented in other technology such as digital logic-based, custom integrated circuit (IC) architecture, if desired. It will also be understood that the present invention may be implemented in cardioverters, defibrillators and the like.

Lead 14 includes an intracardiac electrode 24 located near its distal end and positioned within the right ventricle 16. Electrode 24 is coupled by a lead conductor 14 through an input capacitor 26 to the node 28, and to the input/output terminals of an input/output circuit 30.

Similarly, the lead 15 has a distally located intracardiac electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits necessary for the detection of electrical signals derived from the heart, such as the cardiac electrogram, output from sensors (not shown) connected to the leads 14 and 15, as well as for the application of stimulating pulses to the heart to control its rate as a function thereof under the control of software-implemented algorithms in a Microcomputer Circuit 32.

Microcomputer Circuit 32 comprises an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means of all data first being digitally encoded and then pulse position modulated on a damped RF carrier, as substantially described in U.S. Pat. No. 5,127,404, issued on Jul. 7, 1992, entitled "Telemetry Format for Implantable Medical Device", which is held by the same assignee as the present invention and which is incorporated herein by reference. A reed switch 51 is connected to Input/Output Circuit 30 to enable patient follow-up via disabling the sense amplifier 146 and enabling telemetry and programming functions, as is known in the art.

A Crystal Oscillator Circuit 56, typically a 32,768 Hz crystal-controlled oscillator, provides main timing clock Signals to Digital Controller/Timer Circuit 50. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention, and which is incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VIR, VOOR and VVTR. Further, pacemaker 10 can be programmably configured to operate such that it varies its rate only in response to one selected sensor output, or in response to both sensor outputs, if desired.

Figure 3:
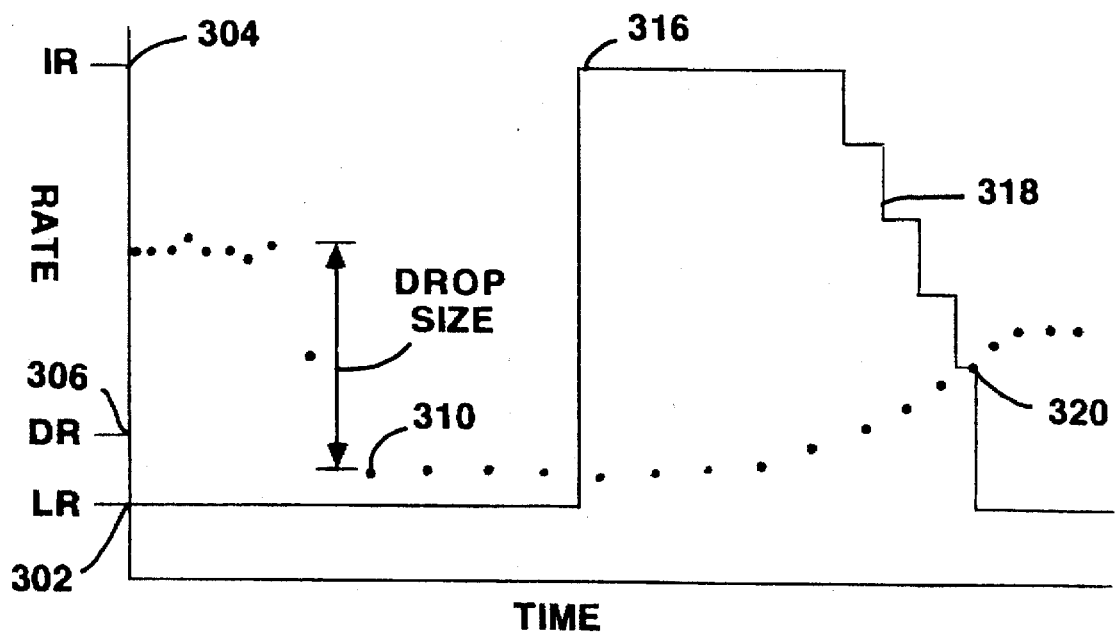
FIG. 3 is a graph of heart rate and pacer rate versus time illustrating the vasovagal syncope detection function of the present invention.

Details of the vasovagal syncope detection feature of the present invention follow below, with reference to FIG. 3. It should be understood that the present invention is not limited to the detection of vasovagal syncope, and it can be used to detect episodes reflective of other S vasodepressor or cardioinhibitory disorders such as carotid sinus syndrome.

A lower rate (LR, 302) is shown—a rate below which the heart will not be allowed to fall (also known as the base escape rate or the base pacing rate of the pacer). This rate may be, for example, 50–70 beats per minute. Also defined are an intervention rate (IR, 304), substantially above the lower rate, and a drop rate (DR, 306), between the lower rate and the intervention rate. The values of all of these rates are programmable by the physician and it is anticipated that the intervention rate should be less than the maximum pacing rate attainable by the pacer, in the case of rate-responsive or dual chamber (e.g. DDD or VDD) pacers.

The intrinsic heart rate is illustrated by means of individual dots, each of which indicate the rate of a detected heartbeat, defined as the reciprocal of the interval separating the beat from the previous beat, and the pacer's escape rate is illustrated by solid line. If the invention is practiced in a single chamber pacemaker (e.g. VVI or AAI), the pacer will be inhibited from delivering pulses when the patient's rate is higher than the pacer's escape rate. If the pacer is an atrial synchronized, dual chamber pacer (e.g. DDD or VDD), the pacer will pace synchronized to the patient's intrinsic rate when the patient's rate is higher than the pacer's escape rate. In dual chamber modes which are synchronized to the atrium, it is contemplated that the atrial heart rate will generally be monitored. For simplicity, it is assumed that the pacer is not set to a rate responsive mode, and that therefore the pacer's escape rate is equal to a fixed lower rate 302.

The pacer stores the intervals associated with successive heart beats, keeping a record of the preceding series of beats. Detection of a vasovagal syncope episode begins at 310, in response to a detected heartbeat (beat "N"), below the drop rate 306. The pacer is then determines whether there has been a sudden, significant rate drop prior to beat "N", by checking to see whether there has been a drop of at least a predetermined drop size, over a preceding series of heart beats. In the illustrated case, the pacer compares beat "N" with beat "N-2", and determines if the rate difference, as measured in beats per minute or in net milliseconds of inter-beat interval change exceeds the defined drop size. A more complicated method of determining whether the detected rate drop is sufficiently rapid, is discussed below in conjunction with FIG. 4. As alternatives, the pacemaker may detect a significant, rapid rate drop by means of a calculation of average rate of change, as discussed above in conjunction with the Sutton patent, or in response to a rate drop from above a threshold rate to below the drop rate, if desired. If the detected rate drop is not sufficiently rapid, the device continues to pace at the lower rate, and the vasovagal syncope detection sequence is aborted.

If the rate drop is sufficiently rapid, the pacer assesses the stability of the slowed rate by monitoring the beats following the beats following beat "N", to determine whether a stable rate is exhibited. A stable rate may be detected, for example, in response to a series of a predetermined number of beats having rates less than the drop rate. A more complicated method of determining whether the detected slowed heart rate is sufficiently stable is discussed below in conjunction with FIG. 4. If the detected lowered heart rate is not sufficiently stable, the device continues to pace at the lower rate, and the vasovagal syncope detection sequence is aborted.

If the detected lowered heart rate is sufficiently stable, therapeutic intervention is triggered. The therapeutic intervention as illustrated is provided by increasing the pacer's escape rate to the intervention rate 304, at 316. In the absence of faster spontaneous heart rates, the escape rate remains at the intervention rate for a programmed period of time and thereafter gradually declines at 318 until the spontaneous heart rate exceeds the pacer's escape rate at 320, at which point the pacer's escape rate is reset to the lower rate. If the patient's spontaneous rate exceeds the intervention rate, the pacer similarly resets its escape rate to the lower rate, and aborts the therapeutic intervention. A more detailed description of the therapeutic intervention illustrated is set forth in U.S. Pat. No. 5,540,728, for a "PACEMAKER WITH VOSOVAGAL SYNCOPE DETECTION" filed on even date with the parent application hereof (U.S. Ser. No. 08/246.647), and is incorporated herein in its entirety.

Figure 4:
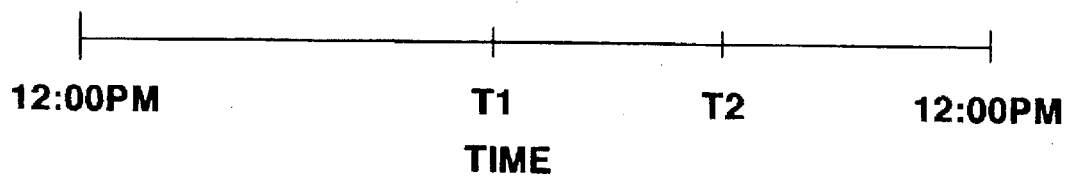
FIG. 4 is a graph of pacer rate versus time illustrating disabling of the vasovagal syncope detection function of the present invention during sleep periods.

To further prevent inappropriate triggering of pacing at an increased rate, the present invention disables the vasovagal syncope detection feature of the present invention while the patient is presumed to be asleep. Such a rate increase could unnecessarily lead to disturbing the patient's sleep by raising his or her heart rate to the intervention rate. This sleep disable feature is illustrated in FIG. 4.

This feature is implemented in the present invention with the use of a diurnal clock in the microcomputer circuit 32 which causes the microcomputer circuit 32 to divide each 24 hour period into a wake period, illustrated as expiring at T1 and a sleep period, illustrated as expiring at T2. The sleep and wake periods are programmed to suit the individual patient's lifestyle. The processor 32 disables the vasovagal syncope detection function during the sleep period extending from T1 to T2.

Figure 5:
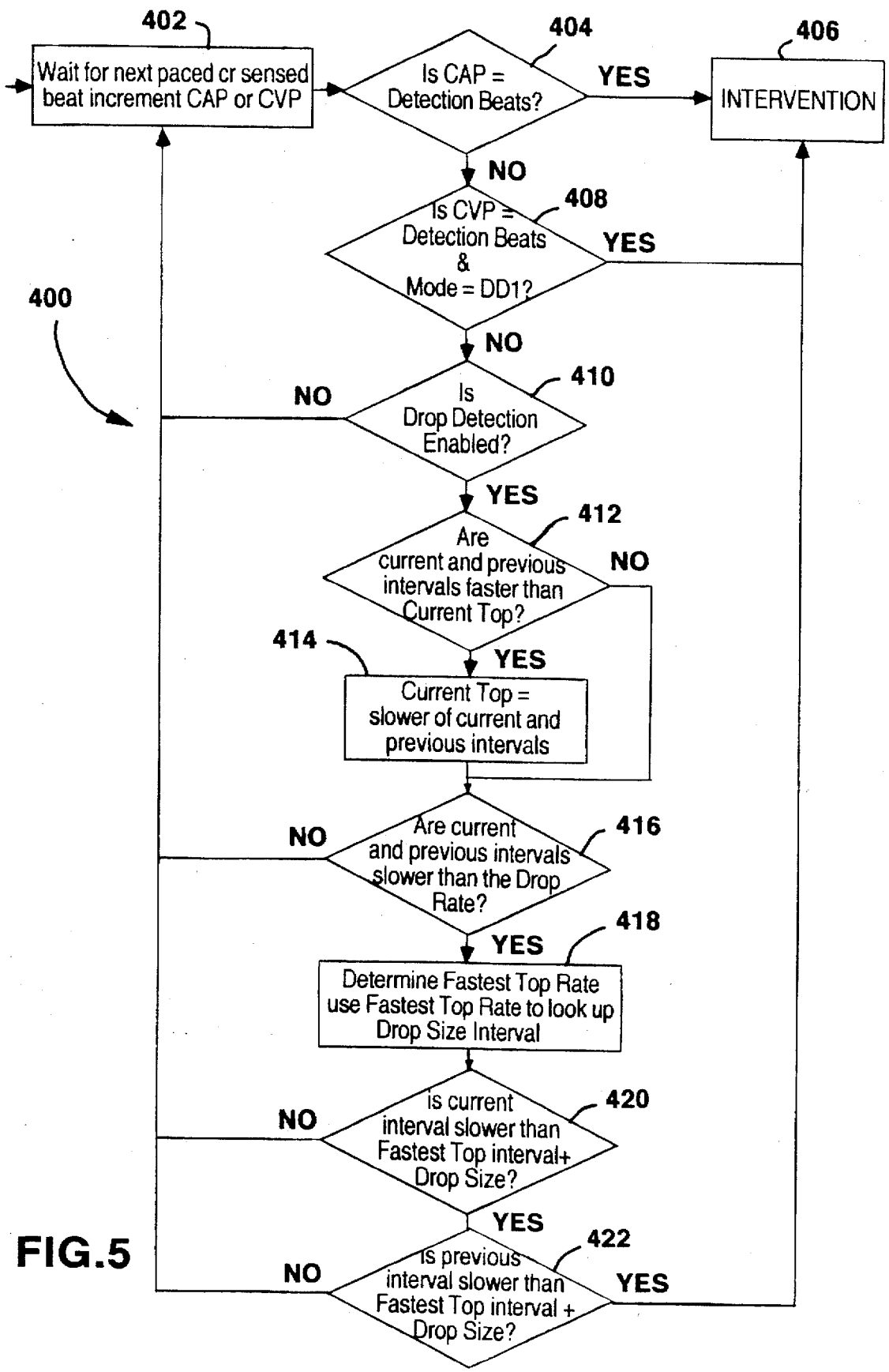
FIG. 5 is a flowchart detailing a the operation of an implantable pacemaker embodying the invention.

FIG. 5 is a flowchart describing a program 400 for implementing a preferred embodiment of the vasovagal syncope detection function of the present invention. For each beat, the "rate" referred to in the following description is the reciprocal of the interval separating it from the previous beat. For ease of understanding, the device's operation is described primarily in terms of comparisons of "rates". However, it should be understood that the device actually stores and processes intervals, and that therefore comparison of rates is actually accomplished in the device software by comparison of stored intervals.

In interpreting this flow chart, it should be understood that the device is programmed to operate in DDD or DDI mode, and employs non-refractory sensed ventricular beats and paced ventricular beats in calculation of rates. However, the invention may also be usefully practiced in devices programmed to VDD, AAI, WI or other modes, with atrial or ventricular beats employed for determination of heart rates. Generally, rate drop is derived by comparing the heart rate following drop to a rate below the drop rate to the highest of 5 stored rates sampled over the previous 2 to 2.5 minutes. Each of the 5 stored rates is the rate of the slower beat in the fastest two beat sequence within a 30 second interval. The fastest of these stored rates is identifies as the highest persistent rate and is used in determining the rate drop.

During the operation of the program 400, counts are kept of the number of consecutive pacing pulses at the base pacing rate, as part of the above-described alternative method of detecting Vasovagal syncope. In devices operating in VVI or AAI modes, successive pacing pulses in the corresponding chamber would correspondingly be counted. In a device programmed to DDD mode, this may be accomplished by simply keeping track of consecutive atrial paces (CAP). In devices programmed to DDI mode, either consecutive atrial paces (CAP) or consecutive ventricular paces (CVP) may be counted. In a device operating in VDD mode, consecutive ventricular paces occurring at the lower rate would have to be separately counted.

At Step 402 CAP is incremented whenever an atrial pace occurs, and reset to zero whenever an atrial sense occurs. Likewise, CVP is incremented whenever a ventricular pace occurs, and reset to zero whenever a ventricular sense occurs. At Step 404 if CAP equals the number of consecutive beats required to indicate detection, the program 400 then advances to Step 406 where the pacemaker 10 can begin interventional therapy, as illustrated in FIG. 3. If CAP does not equal the required number of detection beats, the program 400 advances to Step 408.

At Step 408, if the current pacing mode is DDI and CVP equals the required number of detection beats, intervention is triggered at Step 406. If these conditions are not met, the program advances to Step 410. If the drop detection feature of the pacemaker 10 is enabled, the program continues to Step 412. Otherwise, the program returns to Step 402. The drop detection feature may be disabled due to programming the feature off, or due to the sleep disable function described in conjunction with FIG. 4, above.

As described above, the processor keeps track of heart rates over successive 30 second intervals, identifying the lower rate of the fastest two beat sequence in each 30 second interval. This function is illustrated at Steps 412 and 414. The "Current Top" referred to at Step 412 is initially set equal to the rate of the slower of the first two beats in the 30 second interval underway, and rates of successive beats are compared to the "Current Top". At Step 412, the processor 32 examines the two previous beats to determine whether they are both faster than the "Current Top". If so, the lower rate of the two previous beats is identified as the new "Current Top" at Step 414. The "Current Top" at the expiration of the 30 second interval in effect or on drop of the rate below the Drop Rate, is stored as the "Top Rate" for that interval. If not, the "Current Top" is unchanged.

At Step 416, the processor determines whether the current and previous beats are slower than the Drop Rate. Two successive beats having rates below the drop rate are thus required in order to detect vasovagal syncope, as discussed in conjunction with FIG. 3. Alternatively, a greater number of beats having rates below the Drop rate might be required, or a predetermined proportion of beats having rates below the Drop Rate, might be employed as indicative of a stable, lowered rate, as described in the above-cited patent application by Markowitz et al. If the rates of the two preceding beats are not slower than the Drop Rate, the program returns to Step 402. If the beats have rates slower the Drop Rate, the program advances to Step 418 to begin examining the size of the rate drop.

At step 418, the processor 32 determines which of the preceding five stored "Top Rates", including the top rates stored for the four preceding 30 second intervals and the "Current Top" in effect, is the fastest. This fastest "Top Rate" will be compared to the rate of the most recent beat (second beat having a rate below the Drop Rate) to determine whether the difference is greater than a defined Drop Size.

In a preferred embodiment of the device, it is desired that the physician be able to define the desired rate Drop Size in beats per minute, in conjunction with a defined Drop Rate, also,expressed in beats per minute. However, as discussed above, the device actually operates based on stored intervals, rather than rates. Therefore, the pacer is provided with a stored look-up table, for defining Drop Size Intervals corresponding to the difference in intervals between beats at the fastest "Top Rate" and intervals between beats at the fastest "Top Rate" minus the Drop Size, as expressed in beats per minute. The applicable Drop Size Interval is determined at step 418.

In the programmer used in conjunction with the pacer, the Drop Size Interval look-up table takes the form of a multiple column table, as illustrated in FIG. 6. Drop sizes are listed along the horizontal upper edge and top rates are listed along the left vertical edge, with corresponding Drop Size Intervals listed in columns. In conjunction with programming the Drop Size, only a single column of the table need be loaded via the telemetry circuit 54 into the RAM 42 of the pacer for later use, saving memory capacity in the pacer, and allowing the pacer to determine the Drop Size Interval based only on the fastest "Top Rate", which in turn reduces the number of steps required to determine the Drop Size Interval.

At steps 420 and 422, respectively, the intervals corresponding to the rates of the first two beats below the Drop Rate, identified in Step 416, are compared to the sum of the Drop Size Interval plus the interval corresponding to the fastest "Top Rate", to determine whether these two beats are both at rates less than the fastest "Top Rate" minus the Drop Size as expressed in beats per minute. If so, pacing at an increased rate is initiated at step 406, as discussed above. If not, the pacer returns to step 402 and continues to pace at the lower rate.

Variations and modifications to the present invention are possible given the above disclosure. However, such variations and modifications are intended to be within the scope of the invention claimed by this letters patent. For example, although the preferred embodiment is directed to detection and treatment with respect to vasovagal syncope, the present invention can also be used with respect to neurogenic syncope, vasodepressor and cardioinhibitory disorders, such as carotid sinus syndrome.

We claim:

1. A cardiac pacer comprising:

means for detecting depolarizations of a heart;

means for determining spontaneous heart depolarization rate;

pulse generating means for delivering cardiac pacing pulses at a first pacing rate;

drop detecting means for detecting a rapid drop in spontaneous heart depolarization rate, said drop detecting means comprising means for identifying a highest persistent heart rate over a limited time interval and means for determining whether said spontaneous heart depolarization rate has dropped more than a defined amount from said highest persistent heart rate; and means responsive to a said detected rapid drop in spontaneous heart depolarization rate for causing said pulse generator means to deliver pacing pulses at a second pacing rate higher than said first pacing rate.

2. A cardiac pacer according to claim 1 wherein said means for detecting said highest persistent heart rate comprises means for identifying a fastest sequence of a predetermined number of beats, during said limited time interval.

3. A cardiac pacer according to claim 2 wherein said means for detecting said highest persistent heart rate comprises means for identifying a fastest sequence of two beats, during said limited time interval.

4. A cardiac pacer according to claim 3 wherein said means for detecting said highest persistent heart rate comprises means for identifying a rate of the slowest of said beats in said fastest sequence of two beats, as said highest persistent heart rate.

5. A cardiac pacer according to claim 2 or claim 3 or claim 4 wherein said means for detecting said highest persistent heart rate comprises means for defining a series of time intervals and comprises means for identifying a highest persistent heart rate over said series of defined time intervals.

6. A cardiac pacer according to claim 1 or claim 2 or claim 3 or claim 4 wherein said drop detecting means comprises means for detecting a drop in spontaneous heart rate from said highest persistent heart rate, of greater than a defined drop size.

7. A cardiac pacer according to claim 6 further comprising means for detecting a drop in spontaneous heart rate to a rate below a defined drop rate and wherein said means for causing said pulse generator means to deliver pacing pulses at a second pacing rate comprises means for causing said pulse generator means to deliver pacing pulses at said second pacing rate in response to a said detected rapid drop in spontaneous heart rate in conjunction with a said detected drop in spontaneous heart rate below said drop rate.

8. A cardiac pacer comprising:

means for detecting depolarizations of a heart;

means for determining spontaneous heart depolarization rate;

pulse generating means for delivering cardiac pacing pulses at a first pacing rate;

drop detecting means for detecting a rapid drop in spontaneous heart depolarization rate;

means responsive to a said detected rapid drop in spontaneous heart depolarization rate for causing said pulse generator means to deliver pacing pulses at a second pacing rate higher than said first pacing rate;

means for defining time periods associated with sleeping; and means for disabling said drop detection means during said time periods associated with sleeping.

9. A pacer according to claim 8, wherein said means for defining time periods associated with sleeping comprises means for defining a 24 hour cycle and means for defining said periods associated with sleeping as part of said 24 hour cycle.

10. A cardiac pacer comprising:

means for detecting heart depolarizations;

means for storing heart depolarization intervals;

means for determining spontaneous heart depolarization rate;

pulse generating means for delivering cardiac pacing pulses at a first pacing rate;

rapid rate drop detecting means comprising means for storing a single column or row of a look-up table relating drop sizes and stored heart depolarization intervals to defined changes in depolarization interval such that only a said column or row associated with said selected drop size is stored, means for selecting a said defined change in depolarization interval as a function of a said stored depolarization interval, and means for identifying a rapid rate drop in response to an increase in heart depolarization interval from said stored depolarization interval, of greater than said selected change in depolarization interval; and means responsive to a said identified rapid rate drop for causing said pulse generator means to deliver pacing pulses at a second pacing rate higher than said first pacing rate.

11. A cardiac pacer according to claim 10 further comprising:

means for defining a drop rate independent of determined spontaneous heart rate and means for detecting a drop in spontaneous heart rate to a rate below said defined drop rate and wherein said means for causing said pulse generator means to deliver pacing pulses at a second pacing rate comprises means for causing said pulse generator means to deliver pacing pulses at said second pacing rate in response to a said detected rapid drop in spontaneous heart rate in conjunction with a said detected drop in spontaneous heart rate below said defined drop rate.

12. A cardiac pacer comprising:

means for detecting depolarizations of a heart chamber;

pulse generating means for delivering cardiac pacing pulses at a first pacing rate in absent detected depolarizations of said heart chamber;

means responsive to generation of a series of pacing pulses at said first pacing rate without intervening detected depolarizations of said chamber, for temporarily causing said pulse generating means to generate pacing pulses at a second pacing rate in excess of said first pacing rate.

13. A cardiac pacer according to claim 12 wherein said responsive means comprises means responsive to generation of a predetermined number of pacing pulses at said first pacing rate.

14. A cardiac pacer according to claim 12 wherein said responsive means comprises means for causing said pulse generating means to generate pacing pulses at said second pacing rate for a predetermined time period and means for thereafter causing said pulse generating means to gradually decrement the rate of pacing pulses generated from said second rate to said first rate.

15. A device as set forth in claim 12 wherein said means responsive to detection of pacing pulses comprises;

means to count pacing pulses and for generating a signal value representative of said count, and means to determine if said count of pacing pulses exceeds a predetermined value wihtin a predetermined period of time, and if so to generate a signal to increase the pacing rate such that said device will respond so as to increase the pacing rate, without requiring a drop determination.

16. A device as set forth in claim 15 wherein said means to count pacing pulses signal value representative of said count comprises a total of all pacing pulses counted and said means to count comprises:

means for CAP sensing and means for CVP sensing and means responsive to device mode such that when said device is in DDI mode both said means for CAP and said means for CVP sensing contribute count value signals to said signal value representative of said count but when in DDD mode only CAP sensing but not CAP contribute count value signals to said signal value representative of said count.

17. A method of cardiac pacing, comprising:

detecting depolarizations of a heart;

determining spontaneous heart depolarization rate:

delivering cardiac pacing pulses to said heart at a first pacing rate;

detecting a rapid drop in spontaneous depolarization rate of said heart by identifying a highest persistent heart rate over a limited time interval and determining whether said spontaneous heart depolarization rate has dropped more than a defined amount from said highest persistent heart rate; and in response to a detected rapid drop in spontaneous heart depolarization rate, delivering pacing pulses at a second pacing rate higher than said first pacing rate.

18. A method according to claim 17 wherein detecting said highest persistent heart rate comprises identifying a fastest sequence of a predetermined number of beats, during said limited time interval.

19. A method according to claim 18 wherein said detecting said highest persistent heart rate comprises identifying a fastest sequence of two beats, during said limited time interval.

20. A method according to claim 19 wherein detecting said highest persistent heart rate comprises identifying the rate of the slowest of said beats in said fastest sequence of two beats, as said highest persistent heart rate.

21. A method according to claim 18 or claim 19 or claim 20 wherein detecting said highest persistent heart rate comprises defining a series of time intervals and identifying a highest persistent heart rate, over said series of defined time intervals.

22. A method according to claim 17 or claim 18 or claim 19 or claim 20 wherein detecting a rapid drop comprises detecting a drop in spontaneous heart rate from said highest persistent heart rate, of greater than a defined drop size.

23. A method according to claim 22, further comprising detecting a drop in spontaneous heart rate to a rate below a defined drop rate and wherein said step of delivering pacing pulses at a second pacing rate comprises delivering pacing pulses at said second pacing rate in response to a detected rapid drop in spontaneous heart rate in conjunction with a detected drop in spontaneous heart rate below said drop rate.

24. A method of cardiac pacing, comprising:

defining time periods associated with sleeping;

detecting depolarizations of a heart;

delivering cardiac pacing pulses at a first pacing rate;

detecting a rapid drop in spontaneous heart depolarization rate during time periods outside of said time periods associated with sleeping; and responsive to a detected rapid drop in spontaneous heart depolarization rate, delivering pacing pulses at a second pacing rate higher than said first pacing rate.

25. A method according to claim 24, wherein defining time periods associated with sleeping comprises defining a 24 hour cycle and defining said periods associated with sleeping as part of said 24 hour cycle.

26. A method of cardiac pacing, comprising:

detecting depolarizations of a heart chamber;

delivering cardiac pacing pulses at a first pacing rate absent detected depolarizations of said heart chamber; responsive to delivery of a series of pacing pulses at said first pacing rate without intervening detected depolarizations of said chamber, temporarily delivering cardiac pacing pulses at a second pacing rate in excess of said first pacing rate.

27. A method according to claim 26 wherein said step of temporarily delivering cardiac pacing pulses at said second pacing rate comprises delivering cardiac pacing pulses at said second pacing rate responsive to delivery of a predetermined number of pacing pulses at said first pacing rate.

28. A method according to claim 26, further comprising delivering pacing pulses while gradually decrementing rate of delivery of said pacing pulses from said second pacing rate to said first pacing rate.

* * * * *